United States Patent
Harada et al.

(10) Patent No.: US 9,801,917 B2
(45) Date of Patent: Oct. 31, 2017

(54) COMPOSITION FOR IMPROVING BLOOD SUGAR METABOLISM

(71) Applicant: SUNSTAR INC., Osaka (JP)

(72) Inventors: Kayo Harada, Osaka (JP); Youko Sono, Osaka (JP); Takashi Kusakari, Osaka (JP); Motonobu Matsumoto, Osaka (JP)

(73) Assignee: SUNSTAR INC., Osaka (JP)

( * ) Notice: Subject to any disclaimer, the term of this patent is extended or adjusted under 35 U.S.C. 154(b) by 0 days.

(21) Appl. No.: 14/915,332

(22) PCT Filed: Sep. 2, 2014

(86) PCT No.: PCT/JP2014/072977
§ 371 (c)(1),
(2) Date: Feb. 29, 2016

(87) PCT Pub. No.: WO2015/033898
PCT Pub. Date: Mar. 12, 2015

(65) Prior Publication Data
US 2016/0206675 A1    Jul. 21, 2016

(30) Foreign Application Priority Data
Sep. 3, 2013 (JP) ................ 2013-182408

(51) Int. Cl.
*A01N 65/00* (2009.01)
*A61K 36/44* (2006.01)
*A61K 9/00* (2006.01)

(52) U.S. Cl.
CPC ............ *A61K 36/44* (2013.01); *A61K 9/0053* (2013.01); *A61K 2236/00* (2013.01); *A61K 2236/333* (2013.01); *A61K 2236/53* (2013.01)

(58) Field of Classification Search
CPC ..................................................... A61K 36/00
USPC ......................................................... 424/725
See application file for complete search history.

(56) References Cited

FOREIGN PATENT DOCUMENTS

| CN | 101194921 | 6/2008 |
|---|---|---|
| CN | 102949435 | 3/2013 |
| JP | 9-227398 | 9/1997 |
| JP | 2004-10531 | 1/2004 |
| JP | 2007-314475 | 12/2007 |
| JP | 2009-215253 | 9/2009 |
| JP | 2010-37323 | 2/2010 |
| JP | 2011-37732 | 2/2011 |
| JP | 2013-75874 | 4/2013 |
| JP | 2014-198684 | 10/2014 |
| KR | 10-2010-0054653 | 5/2010 |

OTHER PUBLICATIONS

Database Medline [Online] US National Library of Medicine (NLM), Bethesda, MD, US; May 2012 (May 2012), Deng Hang et al: "Influence of different extracts from persimmon leaves on the antioxidant activity in diabetic mice.", XP002768749, Database accession No. NLM22659658, Abstract.
Xie et al., "Persimmon (*Diospyros kaki* L.) leaves: A review on traditional uses, phytochemistry and pharmacological properties", Journal of Ethnopharmacology, vol. 163: pp. 229-240 (2015).
Extended European Search Report, dated Apr. 19, 2017, in corresponding European Application No. 14841908.8-1466/3042661.
International Search Report dated Nov. 25, 2014 in corresponding (PCT) Application No. PCT/JP2014/072977.
Kubota et al., "Impaired Insulin Signaling in Endothelial Cells Reduces Insulin-Induced Glucose Uptake by Skeletal Muscle", Cell Metabolism, vol. 13, Mar. 2, 2011, pp. 294-307.

*Primary Examiner* — Michael Meller
(74) *Attorney, Agent, or Firm* — Wenderoth, Lind & Ponack, L.L.P.

(57) ABSTRACT

An object of the present invention is to provide a composition for improving blood sugar metabolism, the composition improving and/or enhancing sugar metabolism function in skeletal muscle. The present invention provides a composition for improving blood sugar metabolism, the composition comprising a persimmon leaf extract obtained by a process comprising extracting persimmon leaves with a 40-60% ethyl alcohol-water mixture.

2 Claims, 6 Drawing Sheets

COMPOSITION FOR IMPROVING BLOOD SUGAR METABOLISM

TECHNICAL FIELD

The present invention relates to a composition for improving blood sugar metabolism. More specifically, the present invention relates to a composition for improving blood sugar metabolism comprising a persimmon leaf extract obtained by a process comprising extracting persimmon leaves in a mixed solution of ethyl alcohol and water that are mixed at a specific ratio.

BACKGROUND ART

With an increase of people who lead a life with excess energy intake that is more than the amount necessary for vital activities and that is due to factors, such as intake of high-calorie meals and beverages, a reduced amount of daily exercise, and reduced basal metabolism associated with muscle weakness, the number of young people as well as middle-aged and elderly people who develop diabetes or exhibit insulin resistance is increasing. The aging of fat cells is also known to cause insulin resistance. Elderly people with reduced basal metabolism and a reduced exercise amount also have a high risk of developing diabetes.

In this way, changes in everyday life and a shift towards older societies tend to lead to an explosive increase in diabetic patients every year, and the number of people with abnormal blood sugar metabolism, who are people with pre-diabetes, is also considered to be several times larger than the number of diabetic patients. In fact, similar trends are also apparent from the National Health and Nutrition Examination Survey and Diabetes Survey. An increased diabetic population in Japan is considered to be a serious problem. Under these circumstances, efforts "not to exacerbate an existing pathological condition in diabetic patients" and "not to develop diabetes in insulin-resistant people" are important, because diabetes is a disease that cannot be fundamentally cured.

As such efforts, there are "methods for preventing the onset of diabetes or treating diabetes by controlling the blood sugar level within a normal range." Specifically, there are methods such as diet therapy, exercise therapy, and pharmacotherapy. Methods using one or a combination of these therapies are actually performed according to the circumstances and condition of the target patient. However, it is often difficult to continue diet therapy that restricts calorie intake or exercise therapy that requires performing exercise for a certain period of time or longer. In particular, there are more and more cases in which it is difficult, with the above therapies alone, to treat elderly people who not only have reduced basal metabolism, but also a significantly reduced amount of exercise with significantly reduced exercise capacity. On the other hand, pharmacotherapy also cannot be a satisfactory combating method from the viewpoint of preventing healthcare cost increase, and is difficult to be used as a method for preventing the onset of diabetes.

Accordingly, with a focus on sugar metabolism in skeletal muscle that severely affects blood sugar metabolism, attempts have been made to develop means for dramatically enhancing diabetes onset-preventing effects and diabetes pathology-improving effects by being used alone or together with conventional therapeutic or preventive methods.

One of the physiological functions that lower blood sugar level is a "metabolism function through uptake of blood sugar from blood vessels (blood) into skeletal muscle." The following action is known as a mechanism of this function: "skeletal muscle contraction stimulates phosphorylation (activation) of intracellular AMP kinase, which causes translocation of glucose transporter 4 in the cytoplasm into the cell membrane, thus resulting in blood sugar uptake into skeletal muscle cells." It has also been revealed that that sugar uptake into skeletal muscle cells does not necessarily require skeletal muscle contraction, but is caused by activation of AMP kinase. Accordingly, even when exercise cannot contract skeletal muscle, the function of blood sugar uptake into skeletal muscle is potentially achievable just like exercise is performed. In recent years, while focusing on this point, several "attempts to reduce blood sugar concentration by oral intake of a substance that activates AMP kinase" have been proposed (Patent Literature (PTL) 1 and Patent Literature (PTL) 2).

Further, the following action is also known as another mechanism of sugar uptake from blood vessels (blood) into skeletal muscle cells: "blood insulin binds to an insulin receptor on a cell membrane surface via skeletal muscle interstitial stroma and activation of signaling molecules, such as activation by Akt phosphorylation, causes translocation of glucose transporter 4 in the cytoplasm into the cell membrane, thus resulting in blood sugar uptake into skeletal muscle cells." In this mechanism, the pathway through which insulin is transported from capillary vessels supplying skeletal muscles to skeletal muscle interstitial stroma also plays an important role. It is known that an increase in capillary surface area and blood flow resulting from an increase in diastolic function through e-NOS activation etc. in skeletal muscle capillaries or an increase in capillary density by angiogenesis enhances the transport of insulin into cells, thus improving sugar metabolism (Non-patent Literature 1 (NPL) 1).

The former AMP kinase-mediated mechanism and the latter insulin-mediated mechanism function independently from each other, and both can be expected to exhibit high sugar uptake effects. While these two mechanisms are normally expressed in healthy persons, the latter mechanism is reduced or lost in diabetes patients or insulin-resistant persons. Accordingly, expressing these two mechanisms in concert, or enhancing these two mechanisms, might potentially achieve a condition more similar to that of healthy persons. However, there is no known method that enables both of the mechanisms to be expressed, and a proposal for a specific method for the solution has been desired.

CITATION LIST

PTL

PTL 1: JP2010-37323A
PTL 2: JP2011-37732A

NPL

NPL 1: Cell Metabolism, 13, 294-307, 2011

SUMMARY OF THE INVENTION

Technical Problem

An object of the present invention is to provide a composition for improving blood sugar metabolism that improves and/or enhances sugar metabolism function in skeletal muscle.

Solution to Problem

In view of the above circumstance, the present inventors conducted extensive research, and found that a persimmon leaf extract obtained by a process comprising extracting persimmon leaves using a mixed solution of ethyl alcohol and water that are mixed at a specific ratio can significantly improve and/or enhance sugar metabolism function in skeletal muscle, based on the two mechanisms of AMP kinase-mediated mechanism and insulin-mediated mechanism. The present invention has been accomplished through further research based on this finding.

That is, the present invention typically encompasses the inventions in the following items.

Item 1. A composition for improving blood sugar metabolism, comprising a persimmon leaf extract obtained by a process comprising extracting persimmon leaves with a 40-60% ethyl alcohol-water mixture.

Item 2. The composition for improving blood sugar metabolism according to Item 1, wherein the persimmon leaf extract is obtained by a process comprising: extracting persimmon leaves with a 40-60% ethyl alcohol-water mixture; adsorbing the extract obtained in the above extraction step on a column packed with an octadecylsilyl-bonded silica gel; and performing elution with a 5-10% acetonitrile-water mixture.

Item 3. The composition for improving blood sugar metabolism according to Item 1, wherein the persimmon leaf extract is obtained by a process comprising: extracting persimmon leaves with a 40-60% ethyl alcohol-water mixture; adsorbing an extract obtained in the above extraction step on a column packed with a modified dextran; and performing elution with a 70-100% methyl alcohol-water mixture, or a 60-80% acetone-water mixture.

Item 4. The composition for improving blood sugar metabolism according to any one of Items 1 to 3 that is an oral composition.

Item A-1. A method for improving and/or enhancing blood sugar metabolism, comprising administering to a subject a persimmon leaf extract that is obtained by a process comprising extracting persimmon leaves with a 40-60% ethyl alcohol-water mixture.

Item A-2. The method according to Item A-1, wherein the persimmon leaf extract administered to the subject is obtained by a process comprising: extracting persimmon leaves with a 40-60% ethyl alcohol-water mixture; adsorbing an extract obtained in the above extraction step on a column packed with an octadecylsilyl-bonded silica gel; and performing elution with a 5-10% acetonitrile-water mixture.

Item A-3'. The method according to Item A-1, wherein the persimmon leaf extract administered to the subject is obtained by a process comprising: extracting persimmon leaves with a 40-60% ethyl alcohol-water mixture; adsorbing an extract obtained in the above extraction step on a column packed with a modified dextran; and performing elution with a 70-100% methyl alcohol-water mixture, or a 60-80% acetone-water mixture.

Item B-1. A method for preventing, ameliorating, and/or treating at least one selected from the group consisting of diabetes, hyperglycemia, abnormal glucose tolerance, insulin resistance, arteriosclerosis, obesity, body fat accumulation, dyslipidemia, lifestyle disease, and fat liver, the method comprising administering to a subject a persimmon leaf extract obtained by a process comprising extracting persimmon leaves with a 40-60% ethyl alcohol-water mixture.

Item B-2. The method according to Item B-1, wherein the persimmon leaf extract administered to the subject is obtained by a process comprising: extracting persimmon leaves with a 40-60% ethyl alcohol-water mixture; adsorbing an extract obtained in the above extraction step on a column packed with an octadecylsilyl-bonded silica gel; and performing elution with a 5-10% acetonitrile-water mixture.

Item B-3. The method according to Item B-1, wherein the persimmon leaf extract administered to the subject is obtained by a process comprising: extracting persimmon leaves with a 40-60% ethyl alcohol-water mixture; adsorbing an extract obtained in the above extraction step on a column packed with a modified dextran; and performing elution with a 70-100% methyl alcohol-water mixture, or a 60-80% acetone-water mixture.

Advantageous Effects of Invention

The present invention, which can activate AMP kinase, not only can enhance the blood sugar-lowering effect provided by doing exercise, but also can provide a blood sugar-lowering effect that is equivalent to that provided by doing exercise, even without doing exercise. Furthermore, the present invention, which can enhance skeletal muscle capillary density, can provide an insulin resistance-improvement effect.

As described above, the composition for improving blood sugar metabolism of the present invention can improve and/or enhance sugar metabolism mechanism in skeletal muscle, based on both of an AMP kinase-mediated mechanism and an insulin-mediated mechanism. Accordingly, blood sugar level can be reduced not only in diabetic patients and diabetic pre-patients, but also in people who cannot secure a sufficient amount of exercise, such as elderly people and bed-ridden people, thus preventing the onset of diabetes and improving diabetes pathology.

Further, the composition for improving blood sugar metabolism of the present invention is useful as an exercise effect enhancer that enhances exercise effects by its intake before, during, or after exercise. Furthermore, since the composition for improving blood sugar metabolism of the present invention can activate AMP kinase, anti-aging effects can be expected.

BRIEF DESCRIPTION OF DRAWINGS

FIG. 1 shows the measurements of the expression ratio of phosphorylated AMPK (pAMPK) to total AMPK (tAMPK) of each persimmon leaf extract obtained in Production Example 1 using a mouse skeletal myotube cell line.

FIG. 2 shows the measurements of sugar uptake-promoting activity of persimmon leaf extracts A and C obtained in Production Example 1 using a mouse skeletal myotube cell line.

FIG. 3 shows the measurements of sugar uptake-promoting activity of each fraction obtained in Production Example 2 using a mouse skeletal myotube cell line.

FIG. 4 shows the measurements of sugar uptake-promoting activity of extract C and various compounds contained in persimmon leaves using a mouse skeletal myotube cell line.

FIG. 5 shows measurements of sugar uptake-promoting activity of each fraction obtained in Production Example 3 using a mouse skeletal myotube cell line.

FIG. 6 shows measurements of sugar uptake-promoting activity of each extract obtained in Reference Production Example 1 using a mouse skeletal myotube cell line.

DESCRIPTION OF EMBODIMENTS

Figure 1:
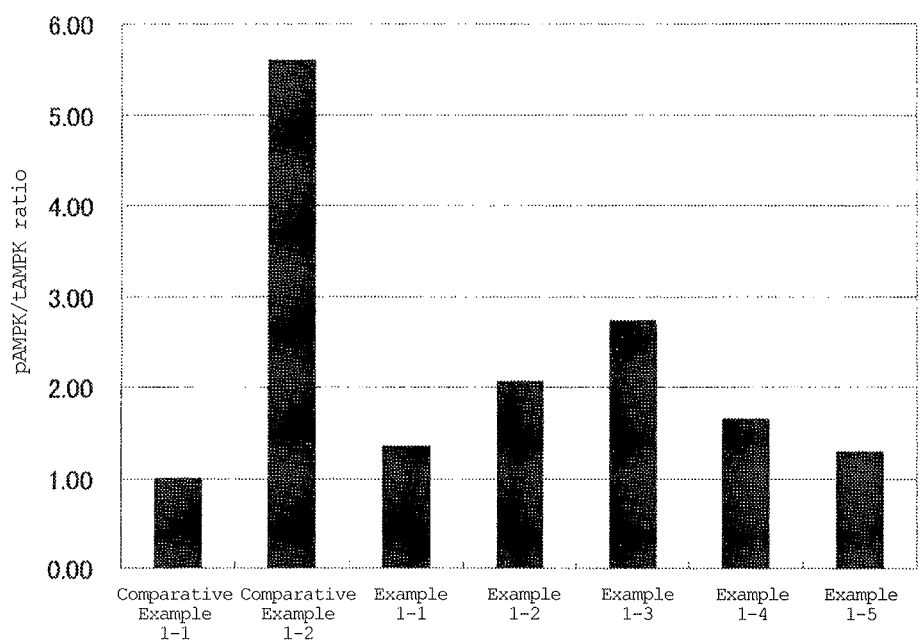
FIG. 1 is a graph showing the results of Test Example 1-1. Specifically.

The present invention is described below in detail.

The composition for improving blood sugar metabolism of the present invention comprises a persimmon leaf extract obtained by a process comprising extracting persimmon leaves with a mixed solution of ethyl alcohol and water that are mixed at a specific ratio.

The persimmon leaves to be extracted are not particularly limited. For example, deciduous leaves of *Diospyros Kaki* Thunb. can be used. Although persimmon leaves before or after falling can be used, using persimmon leaves before falling is preferable. Persimmon leaves to be extracted may be subjected to pretreatment, such as drying, in a usual manner. Examples of methods for pre-treating persimmon leaves include a method comprising washing persimmon leaves, which have been cut from trees, with water, optionally cutting the leaves to an appropriate size (e.g., about 3 mm wide), steaming the leaves with a bamboo steamer, and then drying; a method comprising washing persimmon leaves, which have been cut from trees, with water, optionally cutting the leaves to an appropriate size, and then drying; and the like.

The solution used for extraction of persimmon leaves is a solution obtained by mixing ethyl alcohol and water at a specific ratio (hereinafter referred to as an "ethyl alcohol-water mixture"). The ethyl alcohol-water mixture contains ethyl alcohol in an amount of about 40 to 60% (wt/wt), preferably about 45 to 55% (wt/wt), and more preferably about 50% (wt/wt). Hereinafter, an ethyl alcohol-water mixture with an ethyl alcohol content of x % (wt/wt) is referred to as an "x % ethyl alcohol-water mixture."

The method for extracting persimmon leaves can be any known method, as long as the method uses the ethyl alcohol-water mixture described above. For example, a preferable method comprises extracting dried persimmon leaves with an about 20-fold mass of a 50% ethyl alcohol-water mixture under boiling reflux using a mantle heater for 1 hour.

Further, the persimmon leaf extract may be an extract obtained by a process comprising, after the extraction with an ethyl alcohol-water mixture, concentrating the extract obtained in the extraction step. The concentration method is not particularly limited, and can be suitably selected from known methods. Examples of usable concentration methods include a process comprising, after the extraction with an ethyl alcohol-water mixture, removing the solids from the obtained extract in a usual manner and then removing ethanol from a filtrate obtained by filtration using an evaporator, followed freeze-drying.

Alternatively, the persimmon leaf extract may be an extract obtained by a process comprising, after the extraction with an ethyl alcohol-water mixture, optionally further subjecting the extract obtained in the extraction step to an extraction treatment. Specific examples of such further extraction treatments include a process comprising, after the extraction with an ethyl alcohol-water mixture, dissolving the obtained extract in an about 9-fold mass of purified water, sonicating the solution, and then centrifuging the solution at 10,000 G to collect a supernatant. The extract obtained by concentrating the extract obtained by the extraction with an ethyl alcohol-water mixture may be further subjected to an extraction treatment.

Further, the persimmon leaf extract may be an extract obtained by a process comprising, after the extraction with an ethyl alcohol-water mixture, fractionating the extract using a column.

Known columns can be used as the column for fractionation. Examples of preferable columns include columns packed with an octadecylsilyl-bonded silica gel (such as Purif-Pack Size 200 ODS column), columns packed with modified dextran, and the like.

The eluent used for fractionation can be suitably selected according to the column used. When a column packed with an octadecylsilyl-bonded silica gel is used, a mixed solution of acetonitrile and water (hereinafter referred to as an "acetonitrile-water mixture") is preferably used. When a column packed with modified dextran is used, a mixed solution of methyl alcohol and water (hereinafter referred to as a "methyl alcohol-water mixture") and a mixed solution of acetone and water (hereinafter referred to as an "acetone-water mixture") are preferably used. Hereinafter, an acetonitrile-water mixture with an acetonitrile content of x % is referred to as an "x % acetonitrile-water mixture;" a methyl alcohol-water mixture with a methyl alcohol content of x % is referred to as an "x % methyl alcohol-water mixture;" and an acetone-water mixture with an acetonitrile content of x % is referred to as an "x % acetone-water mixture."

The fractionation conditions (e.g., flow rate) are not particularly limited, and can be suitably set according to the column and eluent used.

Examples of preferable fractionation methods include the following. When the fractionation is performed using a column packed with an octadecylsilyl-bonded silica gel, a preferable fractionation method is, for example, a step-gradient fractionation method comprising adsorbing the extract, which is obtained by the extraction with an ethyl alcohol-water mixture, on a column packed with an octadecylsilyl-bonded silica gel and performing elution while increasing the acetonitrile content of the acetonitrile-water mixture stepwise from 0% by about 1 to 10%. Fractions obtained by elution using 1-10% acetonitrile-water mixtures in this method are preferable in view of their high effects of improving and/or enhancing sugar metabolism function. Fractions obtained by elution using 5-10% acetonitrile-water mixtures are more preferable in view of their particularly high effects of improving and/or enhancing sugar metabolism function. In particular, the fraction obtained by elution with a 5% acetonitrile-water mixture and the fraction obtained by elution with a 10% acetonitrile-water mixture, which are obtained by successive elution with a 0% acetonitrile-water mixture (that is, water), 5% acetonitrile-water mixture, and 10% acetonitrile-water mixture, are more preferable in view of their very high effects of improving and/or enhancing sugar metabolism function. Among these, the fraction obtained by elution with the 5% acetonitrile-water mixture is particularly preferable in view of its particularly high effects of improving and/or enhancing sugar metabolism function.

When the fractionation is performed using a column packed with modified dextran, a preferable fractionation method is, for example, a step-gradient fractionation method comprising adsorbing an extract obtained by the extraction with an ethyl alcohol-water mixture on a column packed with a modified dextran and performing elution while increasing the methyl alcohol content of a methyl alcohol-water mixture stepwise from 0% by about 10 to 20%. A method further comprising elution with an about 60-80% acetone-water mixture after completion of the elution with a 100% methyl alcohol-water mixture (that is, methyl alcohol) is also preferable. Fractions obtained by elution with about 40-100% methyl alcohol-water mixture(s) and about 60-80% acetone-water mixture(s) in this method are preferable in view of their high effects of improving and/or enhancing sugar metabolism function. Fractions obtained by elution with about 80-100% methyl alcohol-water mixture(s) and an about 70% acetone-water mixture are more preferable in view of their particularly high effects of improving and/or enhancing sugar metabolism function. In particular, the fraction obtained by elution with a 100% methyl alcohol-water mixture and the fraction obtained by elution with a 70% acetone-water mixture, which are obtained by successive elution with a 0% methyl alcohol-water mixture (that is, water), 20% methyl alcohol-water mixture, 40% methyl alcohol-water mixture, 60% methyl alcohol-water mixture, 80% methyl alcohol-water mixture, 100% methyl alcohol-water mixture (that is, methyl alcohol), and 70% acetone-water mixture, are more preferable in view of their particularly high effects of improving and/or enhancing sugar metabolism function.

The composition for improving blood sugar metabolism of the present invention may be the persimmon leaf extract itself, or may contain other components in addition to the persimmon leaf extract. Examples of such other components include pharmaceutically or food-hygienically acceptable carriers, and the like.

The composition for improving blood sugar metabolism can be used as an oral composition. The oral composition can be formulated into drugs and quasi drugs as well as functional foods or beverages, foods for patients, foods for specified health uses (FOSHU), foods with nutrient function claims (FNFC), dietary supplement foods, foods for exercise therapy, foods for slimming, and the like with the concepts of preventing or ameliorating diabetes, hyperglycemia, abnormal glucose tolerance, insulin resistance, arteriosclerosis, obesity, body fat accumulation, dyslipidemia, lifestyle disease, fatty liver, and the like, enhancing sugar metabolism, or providing anti-aging and like physiological functions.

The form of the composition for improving blood sugar metabolism is not particularly limited. When used as an oral composition, the composition can be formed into hard capsules, soft capsules, supplements, chewable tablets, beverages, powdered beverages, granules, films, and the like. When used as a food or beverage, the composition may be formed into beverages such as tea beverages, sports drinks, beauty drinks, fruit-juice drinks, carbonated beverages, alcoholic beverages, soft drinks, jelly beverages, and concentrated beverages for use after being diluted with water, hot water, carbonated water, or the like; dried solids that are ingested after being dissolved or suspended in water, hot water, or the like, such as powders, granules, and tablets; confectionaries such as tablet confectionery, jellies, snacks, baked goods, fritters, cakes, chocolates, gums, candies, and gummy candies; soups, noodles, rice, cereals, and like foods. For use in daily life, supplements, chewable tablets, single-shot drinks, and like forms are preferable. For intake with the purpose of enhancing exercise effects, beverage forms such as sports drinks are the most preferable. Further, these oral compositions can be provided to consumers in the form of packed foods that are placed in containers. The containers to be used are not particularly limited, as long as they can be sealed.

When in the form of an oral solid preparation such as tablets, granules, and capsules, or an oral liquid preparation such as internal liquid preparations and syrups, the oral composition preferably contains the composition for improving blood sugar metabolism in an amount of about 0.01 to 95 mass %, preferably about 5 to 90 mass %, and most preferably about 10 to 80 mass %, on a dry weight basis, based on the total amount of the oral composition. When the oral composition is in a form other than the above, the oral composition preferably contains the composition for improving blood sugar metabolism in an amount of about 0.001 to 50 mass %, preferably about 0.005 to 30 mass %, and most preferably about 0.01 to 10 mass %.

The present invention further provides a method for improving and/or enhancing blood sugar metabolism, the method comprising administering to a subject the composition for improving blood sugar metabolism of the present invention.

Further, the present invention provides a method for preventing, ameliorating and/or treating diabetes, hyperglycemia, abnormal glucose tolerance, insulin resistance, arteriosclerosis, obesity, body fat accumulation, dyslipidemia, lifestyle disease, fatty liver, and the like, the method comprising administering to a subject the composition for improving blood sugar metabolism of the present invention.

EXAMPLES

The present invention is described below in further detail with reference to Examples. However, the scope of the invention is not limited to these Examples. In the Examples below, all percentages are by mass unless otherwise specified.

Production Example 1: Preparation of Persimmon Leaf Extracts Using Ethyl Alcohol-Water Mixtures About 10 g of domestic persimmon leaves that had been dried and cut were extracted with a 20-fold mass of various solvents. The following five types of solvents were used for the extraction: purified water, a 25% (wt/wt) ethyl alcohol-water mixture, a 50% (wt/wt) ethyl alcohol-water mixture, a 75% (wt/wt) ethyl alcohol-water mixture, and ethyl alcohol. The extraction of persimmon leaves was performed under boiling reflux for 1 hour using a reflux extractor. After the extraction, large insoluble matter was removed using 110-mesh nylon. Filtration was then performed using Qualitative Filter Paper No. 1 (produced by Advantech Co., Ltd.). When extraction was performed using a solvent containing ethyl alcohol, the obtained filtrate was freeze-dried after ethyl alcohol was removed using an evaporator. When extraction was performed using purified water, the extract obtained by filtration was directly freeze-dried.

The extracts obtained using the solvents are hereinafter referred to as extract A (extract obtained by extraction with purified water), extract B (extract obtained by extraction with a 25% (wt/wt) ethyl alcohol-water mixture), extract C (extract obtained by extraction with a 50% (wt/wt) ethyl alcohol-water mixture), extract D (extract obtained by extraction with a 75% (wt/wt) ethyl alcohol-water mixture), and extract E (extract obtained by extraction with ethyl alcohol).

Test Example 1: Evaluation of Sugar Metabolism-Improving Effects of Persimmon Leaf Extracts (Extracts A to E)

The sugar metabolism-improving effects of the persimmon leaves extracts obtained in Production Example 1 were evaluated. For the evaluation of the sugar metabolism-improving effects, AMP kinase phosphorylation activity in a mouse skeletal myotube cell line (C2C12 cells) was measured, and sugar uptake-promoting activity of extracts A and C was also measured.

Test Example 1-1: Measurement of AMP Kinase Phosphorylation Activity

Persimmon leaf extracts A to E (powders) that had been dissolved in media to a final concentration of 0.02% were used as samples (Examples 1-1 to 1-5). A medium without any addition was used as a negative control (Comparative Example 1-1). A medium containing AICAR (final concentration: 2 mM) was used as a positive control (Comparative Example 1-2). Subsequently, a mouse skeletal myotube cell line (C2C12 cells) was seeded onto a 6-well cell culture plate and cultured in a DMEM medium containing 10% fetal bovine serum and a 1% antibacterial agent at 37° C., 5% carbon dioxide for 3 days.

When the cells became confluent, the medium was replaced with a DMEM medium containing 1% fetal bovine serum, and the cells were further cultured and fully differentiated. After the medium was again replaced with a fresh medium, the samples of Examples 1-1 to 1-5 and Comparative Examples 1-1 to 1-2 were added, and the cells were cultured at 37° C., 5% carbon dioxide. After the cells were washed with PBS (−) twice, 150 μL of a cell lysis buffer containing a phosphatase inhibitor, a protease inhibitor, and PMSF was added, and each cell lysate was collected with a cell scraper.

The cell lysate was sonicated and then centrifuged to obtain a supernatant. The supernatant was stored at −80° C. until it was subjected to measurement. The protein concentration of each supernatant was measured. The protein concentration in each sample was adjusted to the same level. After the protein concentration of each supernatant was adjusted, a sample buffer (available from Thermo Scientific) was added and the protein was heat-denatured. The resulting product was used in the following Western blotting.

Western blotting was performed in the following manner. First, after SDS-PAGE using 7.5% electrophoresis gel, the protein was transferred to a nitrocellulose membrane using an iBlot. As primary antibodies, phosphorylated AMPK antibody (CST) and total AMPK (CST) were diluted 1000-fold with TBST containing 5% BSA or skim milk. While the temperature was maintained at 4° C., a reaction was allowed to proceed on a shaker overnight. Subsequently, after the nitrocellulose membrane was washed well, an HRP-labeled secondary antibody (CST, 1:5000 or Santa Cruz, 1:10,000) was allowed to react with TBST containing 5% skim milk at room temperature for 1 hour. Further, after the nitrocellulose membrane was washed well, Western blots were developed with a SuperSignal West Dura Extended Duration Substrate (produced by Thermo Scientific) or an ECL Plus Western Blotting Detection System (produced by GE Healthcare). Chemiluminescence was detected using a CCD camera imager (produced by GE Healthcare). The degree of the activity was expressed as a relative value with the value of the negative control being defined as 1. Table 1 and FIG. 1 show the measurement results.

TABLE 1

| | Samples | | | | | | |
|---|---|---|---|---|---|---|---|
| | Comparative Example 1-1 No addition | Comparative Example 1-2 AICAR | Comparative Example 1-1 Extract A | Comparative Example 1-2 Extract B | Comparative Example 1-3 Extract C | Comparative Example 1-4 Extract D | Comparative Example 1-5 Extract E |
| pAMPK/ tAMPK ratio | 1.00 | 5.60 | 1.35 | 2.06 | 2.72 | 1.65 | 1.29 |

Table 1 and FIG. 1 clearly show that Example 1-3 (extract C) had the highest AMP kinase phosphorylation activity, and that Example 1-2 (extract B) had the second highest. The above results suggest that the AMP kinase phosphorylation activity of the obtained extracts varies depending on the ratio of ethyl alcohol in the ethyl alcohol-water mixture used for the extraction of persimmon leaves.

Test Example 1-2: Measurement of Sugar Uptake-Promoting Activity Using Skeletal Myotube Cells Sugar uptake-promoting activity of extract C, which exhibited the highest AMP kinase phosphorylation activity in the above Test Example 1, and extract A, which exhibited a low AMP kinase phosphorylation activity, was measured by the following method using a mouse skeletal myotube cell line (C2C12 cells).

Mouse skeletal myoblasts (C2C12 cells) were cultured in high-glucose DMEM (5790), and the cells were seeded and cultured in a black microtiter plate (produced by Falcon) at a concentration of 5000 cells/200 μL/well. The cells differentiated into myotubes were used for this experiment. Extract A and extract C obtained in the above Production Example 1 and adjusted to final concentrations of 0.02% and 0.05% were used as samples (Examples 2-1 to 2-4). A medium without any addition (Comparative Example 2-1) was used as a negative control. A medium containing insulin (10 nM) (Comparative Example 2-2) was used as a positive control.

Figure 2:
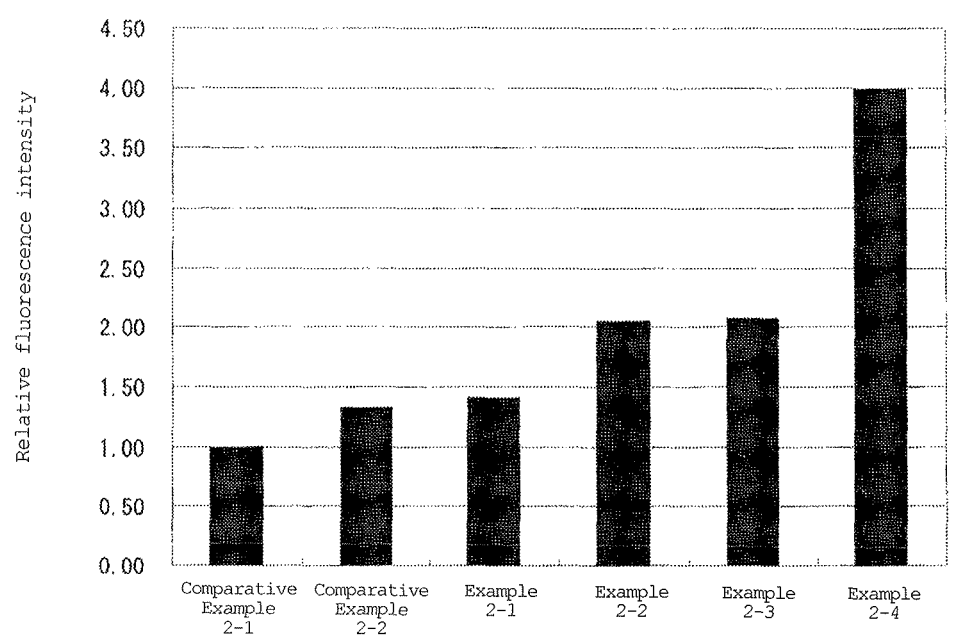
FIG. 2 is a graph showing the results of Test Example 1-2. Specifically.

On the day of the experiment, after the media were replaced with low-glucose DMEM (6047), starvation was performed. The media were then replaced with media containing the samples of Examples 2-1 to 2-4 and Comparative Examples 2-1 to 2-2 dissolved therein, and incubation was performed for 60 minutes. After the treatment, the media were removed and replaced with low-glucose DMEM containing 100 µM of a fluorescently labeled nonhydrolyzable sugar analog, 6-(N-(7-nitrobenz-2-oxa-1,3-diazol-4-yl)amino)-6-deoxyglucose (6-NBDG; produced by Invitrogen) dissolved therein. After the reaction was allowed to proceed for 30 minutes, the medium was removed. After washing with PBS, the fluorescence was measured at 444 nm/538 nm emission using a fluorescent plate reader. Table 2 and FIG. 2 show the results.

stepwise by 5%, elution was performed with the acetonitrile-water mixture of each concentration for 10 minutes. After elution was performed with a 20% acetonitrile-water mixture for 10 minutes, the elution was terminated. Subsequently, each eluate was concentrated with an evaporator, and then freeze-dried to obtain a fraction.

Hereinafter, the fractions obtained by elution with the eluents are referred to as fraction A (fraction obtained by elution with purified water, fraction B (fraction obtained by elution with a 5% acetonitrile-water mixture), fraction C (fraction obtained by elution with a 10% acetonitrile-water mixture), fraction D (fraction obtained by elution with a 15% acetonitrile-water mixture), and fraction E (fraction obtained by elution with a 20% acetonitrile-water mixture).

TABLE 2

| | Sample | | | | | |
|---|---|---|---|---|---|---|
| | Comparative Example 2-1 No addition | Comparative Example 2-2 Insulin | Example 2-1 Extract A 0.02% | Example 2-2 Extract C 0.02% | Example 2-3 Extract A 0.05% | Example 2-4 Extract C 0.05% |
| Relative fluorescence intensity | 1.00 | 1.32 | 1.40 | 2.05 | 2.07 | 3.99 |

Table 2 and FIG. 2 clearly show that Example 2-4 (extract C) exhibits extremely high sugar uptake-promoting activity in skeletal myotube cells. The results of Examples 2-2 and 2-4 suggest that sugar uptake-promoting activity is dependent on the concentration.

The above results of Test Example 1 clearly show that a persimmon leaf extract obtained by extracting persimmon leaves using a mixed solution of water and ethanol alcohol in specific proportions has high AMP kinase phosphorylation activity and sugar uptake-promoting activity.

Production Example 2: Fractionation of Extract C Using ODS Column

After extract C (freeze-dried product) obtained in the above Production Example 1 was dispersed in a 9-fold mass of distilled water, the solution was sonicated and then centrifuged at 10,000 G to obtain a supernatant. The obtained supernatant was adsorbed on a Purif-Pack Size 200 ODS column. As mobile phases for elution, purified water and acetonitrile-water mixtures were used. The flow rate was set to 60 ml/min. Elution was first performed with purified water for 10 minutes, and then with a 5% acetonitrile-water mixture for 10 minutes. Thereafter, while the acetonitrile content of the acetonitrile-water mixture was increased With the mass of extract C applied being defined as 100%, the yield of fraction A was about 58%, the yield of fraction B was about 17%, the yield of fraction C was about 15%, and fractions D and E were hardly collected. The yield of the precipitated components (insoluble matter) after centrifugation was about 19%.

Test Example 2: Measurement of the Sugar Uptake-Promoting Activity Using Skeletal Myotube Cells The sugar uptake-promoting activity, in skeletal myotube cells, of each of extract C (Example 3-1) obtained in the above Production Example 1, and fractions A to C and insoluble matter (Example 3-5) obtained in the above Production Example 2 (Examples 3-2 to 3-4) was measured in the same manner as in Test Example 1-2. Further, as in Test Example 1-2, a medium with no addition was used as a negative control (Comparative Example 3-1), and a medium containing insulin (10 nM) (Comparative Example 3-2) was used as a positive control. The samples of Examples 3-1 to 3-5 were adjusted to a final concentration of 0.02 mass %. Table 3 and FIG. 3 show the measurement results.

TABLE 3

| Sample | Comparative Example 3-1 No addition | Comparative Example 3-2 Insulin | Example 3-1 Extract C | Example 3-2 Fraction A | Example 3-3 Fraction B | Example 3-4 Fraction C | Example 3-5 Insoluble matter |
|---|---|---|---|---|---|---|---|
| Relative fluorescence intensity | 1.00 | 1.25 | 1.79 | 1.37 | 2.91 | 2.20 | 1.48 |

Figure 3:
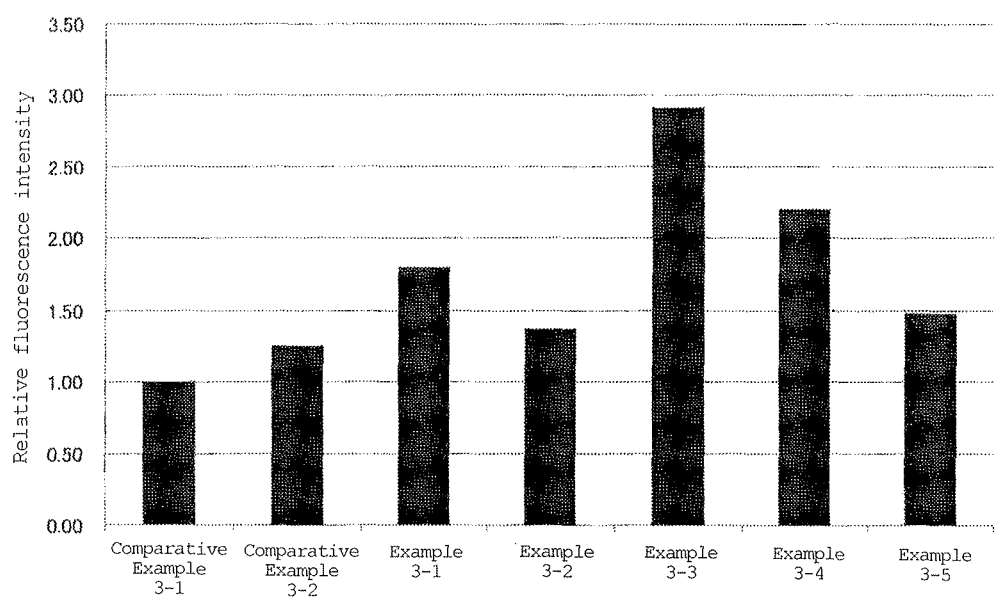
FIG. 3 is a graph showing the results of Test Example 2. Specifically.

As is clear from Table 3 and FIG. 3, the results confirmed that Example 3-3 (fraction B) and Example 3-4 (fraction C) have higher sugar uptake-promoting activity than Example 3-1 (extract C). In particular, Example 3-3 (fraction B) was confirmed to have very high sugar uptake-promoting activity.

Figure 4:
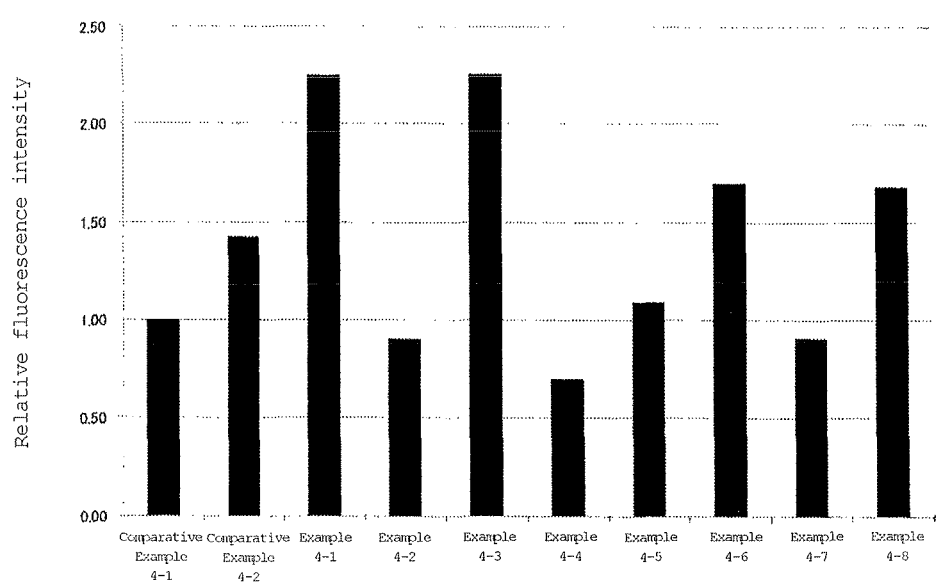
FIG. 4 is a graph showing the results of Test Example 3. Specifically.

Test Example 3: Measurement of the Sugar Uptake-Promoting Activity Using Skeletal Myotube Cells The sugar uptake-promoting activity, in skeletal myotube cells, of extract C obtained in the above Production Example 1 (Example 4-1) and seven compounds known to be contained in persimmon leaves (Example 4-2 to 4-8), i.e., kaempferol-3-O-glucoside, quercetin-3-O-glucoside, quercetin-3-O-galactoside, (+)-catechin, epigallocatechin gallate, rutin, and gallic acid was measured in the same manner as in Test Example 1-2. Further, as in Test Example 1-2, a medium with no addition was used as a negative control (Comparative Example 4-1), and a medium with insulin (10 nM) was used as a positive control (Comparative Example 4-2). The samples obtained in Example 4-1 to 4-8 were adjusted to a final concentration of 0.01 mass %. Table 4 and FIG. 4 show the measurement results.

TABLE 4

| Sample | Comparative Example 4-1 Control | Comparative Example 4-2 Insulin | Example 4-1 Extract C | Example 4-2 Kaempferol-3-glucoside | Example 4-3 Quercetin-3-glucoside |
|---|---|---|---|---|---|
| Relative fluorescence intensity | 1.00 | 1.43 | 2.26 | 0.91 | 2.26 |

| Sample | Example 4-4 Quercetin-3-galactoside | Example 4-5 (+)-catechin | Example 4-6 Epigallocatechin gallate | Example 4-7 Rutin | Example 4-8 Gallic acid |
|---|---|---|---|---|---|
| Relative fluorescence intensity | 0.70 | 1.09 | 1.70 | 0.91 | 1.69 |

As is clear from Table 4 and FIG. 4, Example 4-3 (quercetin-3-O-glucoside), Example 4-6 (epigallocatechin gallate), and Example 4-8 (gallic acid) exhibited sugar uptake-promoting activity as high as Example 4-1 (extract C), whereas the other compounds exhibited lower activity than Example 4-1.

Quercetin-3-O-glucoside, epigallocatechin gallate, and gallic acid, which exhibited high activity in Table 4 and FIG. 4, were not contained in high proportions in extract C. Accordingly, although these components may contribute to some extent, the main active ingredient of extract C is suggested to be something other than these components.

Production Example 3: Fractionation of Extract C Using Sephadex LH-20 Column After extract C (freeze-dried product) obtained in the above Production Example 1 was dispersed in a 9-fold mass of distilled water, the dispersion was sonicated and then centrifuged at 10,000 G to obtain a supernatant. The obtained supernatant was adsorbed on a Sephadex LH-20 column (produced by GE Healthcare Japan). As mobile phases for elution, purified water, methyl alcohol-water mixture, and methyl alcohol were used. The flow rate was set to 20 ml/min. Elution was first performed with purified water for 10 minutes, and then with a 20% methyl alcohol-water mixture for 10 minutes. Thereafter, while the methyl alcohol content of the methyl alcohol-water mixture was increased stepwise by 20%, elution was performed with the methyl alcohol-water mixture of each concentration for 10 minutes. After completion of the elution with methyl alcohol for 10 minutes, elution was further performed using 600 mL of a 70% acetone-water mixture as a mobile phase. Thereafter, each eluate was concentrated with an evaporator, and then freeze-dried to obtain a fraction.

The fractions obtained by elution with the eluents are hereinafter referred to as fraction F (fraction obtained by elution with purified water), fraction G (fraction obtained by elution with a 20% methyl alcohol-water mixture), fraction H (fraction obtained by elution with a 40% methyl alcohol-water mixture), fraction I (fraction obtained by elution with a 60% methyl alcohol-water mixture), fraction J (fraction obtained by elution with a 80% methyl alcohol-water mixture), fraction K (fraction obtained by elution with methyl alcohol), and fraction L (fraction obtained by elution with a 70% acetone-water mixture).

With the mass of extract C applied being defined as 100%, the yield of fraction F was about 65%, the yield of fraction G was about 2%, the yield of fraction H was about 5%, the yield of fraction I was about 2%, the yield of fraction J was about 5%, the yield of fraction K was about 2%, and the yield of fraction L was about 6%. The yield of the components that were not eluted by the elution (insoluble matter) was about 13%.

Figure 5:
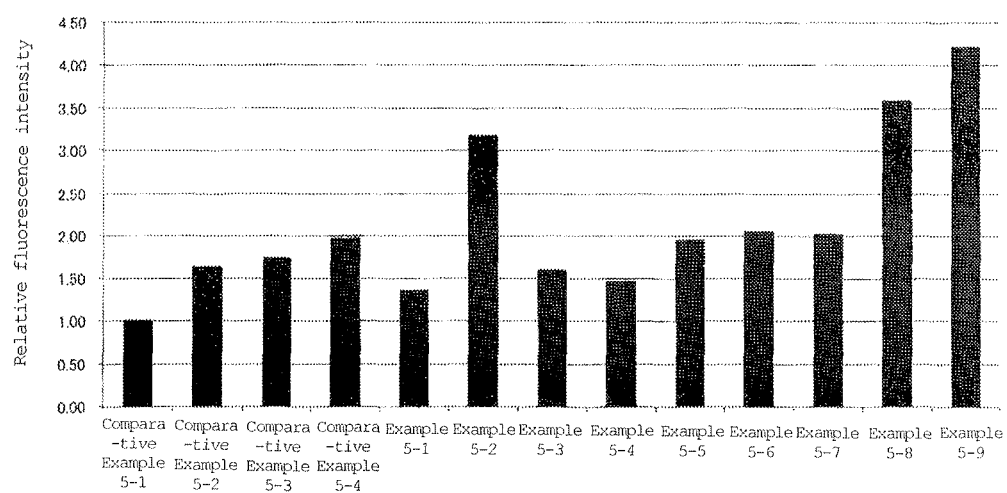
FIG. 5 is a graph showing the results of Test Example 4. Specifically.

Test Example 4: Measurement of Sugar Uptake-Promoting Activity Using Skeletal Myotube Cells The sugar uptake-promoting effects of extract C obtained in the above Production Example 1 (Example 5-1), fraction B obtained in the above Production Example 2 (Example 5-2), and fractions F to L (Examples 5-3 to 5-9) obtained in the above Production Example 3 on skeletal myotube cells were measured in the same manner as in Test Example 2. A medium with no addition was used as a negative control (Comparative Example 5-1), and media with insulin (10 nM) (Comparative Example 5-2), with insulin (100 nM) (Comparative Example 5-3), and with AICAR (final concentration: 3 mM) (Comparative Example 5-4) were used as positive controls. The samples of Examples 5-1 to 5-9 were adjusted to a final concentration of 0.02 mass %. Table 5 and FIG. 5 show the results.

extract obtained using 5° C. purified water), 30C-1 (an extract obtained using 30° C. purified water), 60C-1 (an extract obtained using 60° C. purified water), and 80C-1 (an extract obtained using 80° C. purified water).

Further, the residues collected above were extracted using a reflux extractor under boiling reflux for 1 hour. After the extraction, large insoluble matter was removed using 110-mesh nylon. The extract was filtered using Qualitative Filter Paper No. 1 (produced by Advantech Co., Ltd.), and the filtrate was freeze-dried.

Hereinafter, the extracts from the residues obtained using purified water of the various set temperatures are hereinafter referred to as 5C-2 (an extract from the residue obtained using 5° C. purified water), 30C-2 (an extract from the residue obtained using 30° C. purified water), 60C-2 (an extract from the residue obtained using 60° C. purified water), and 80C-2 (an extract from the residue obtained using 80° C. purified water).

Further, about 10 g of domestic persimmon leaves that had been dried and cut were mixed with a 20-fold mass of 100° C. purified water, and extracted under boiling reflux

TABLE 5

| | Sample | | | | | | |
|---|---|---|---|---|---|---|---|
| | Comparative Example 5-1 Control | Comparative Example 5-2 Insulin 10 nM | Comparative Example 5-3 Insulin 100 nM | Comparative Example 5-4 AICAR 3 mM | Example 5-1 Extract C | Example 5-2 Fraction B | Example 5-3 Fraction F |
| Relative fluorescence intensity | 1.00 | 1.62 | 1.74 | 1.96 | 1.35 | 3.17 | 1.59 |

| | Sample | | | | | |
|---|---|---|---|---|---|---|
| | Example 5-4 Fraction G | Example 5-5 Fraction H | Example 5-6 Fraction I | Example 5-7 Fraction J | Example 5-8 Fraction K | Example 5-9 Fraction L |
| Relative fluorescence intensity | 1.46 | 1.95 | 2.05 | 2.01 | 3.59 | 4.21 |

As is clear from Table 5 and FIG. 5, the results confirmed that Example 5-8 (fraction K) and Example 5-9 (fraction L) had higher sugar uptake-promoting activity than Example 5-2 (fraction B).

Reference Production Example 1: Preparation of Persimmon Leaf Extract by a Two-Stage Extraction Method Using Different Temperatures As a method other than extraction using an ethyl alcohol-water mixture, a persimmon leaf extract was prepared by using the following two-stage extraction method using different temperatures.

After 10 g of domestic persimmon leaves that had been dried and cut were mixed with a 20-fold mass of purified water of each set temperature and gently stirred, the mixture was allowed to stand for 1 hour. Subsequently, after the residue was collected using 110-mesh nylon, the filtrate was freeze-dried. The temperatures of purified water were set to 5° C., 30° C., 60° C., and 80° C.

Hereinafter, the extracts obtained using purified water of the various set temperatures are referred to as 5C-1 (an using a reflux extractor for 2 hours. After the extraction, the residue was removed using 110-mesh nylon. The extract was filtered using Qualitative Filter Paper No. 1 (produced by Advantech Co., Ltd.), and the filtrate was freeze-dried. The extract obtained in this manner is hereinafter referred to as 100 C.

Figure 6:
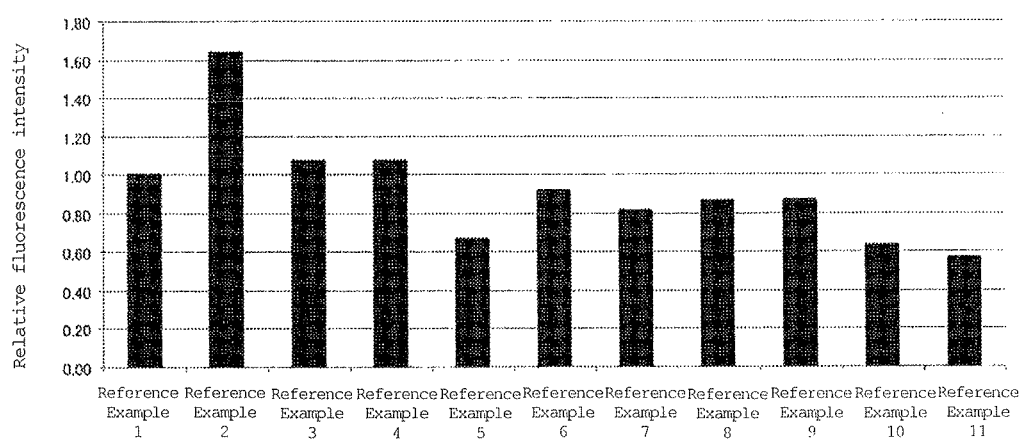
FIG. 6 is a graph showing the results of Reference Test Example 1. Specifically.

Reference Test Example 1: Measurement of Sugar Uptake-Promoting Activity Using Skeletal Myotube Cells The sugar uptake-promoting activity, in skeletal myotube cells, of 30C-1 to 80C-1 (Reference Examples 3 to 6), 100C (Reference Example 7), and 30C-2 to 80C-2 (Reference Examples 8 to 11) obtained in the above Reference Production Example 1, and fraction B obtained in the above Production Example 2 (Reference Example 2) was measured in the same manner as in Test Example 1-2. Further, as in Test Example 5, a medium with no addition (Reference Example 1) was used as a negative control. The samples of Reference Examples 3 to 11 were adjusted to a final concentration of 0.02 mass %. Table 6 and FIG. 6 show the measurement results.

TABLE 6

| | Sample | | | | | |
|---|---|---|---|---|---|---|
| | Reference Example 1 No addition | Reference Example 2 Fraction B | Reference Example 3 5C-1 | Reference Example 4 30C-1 | Reference Example 5 60C-1 | Reference Example 6 80C-1 |
| Relative fluorescence intensity | 1.00 | 1.64 | 1.07 | 1.07 | 0.67 | 0.92 |

| | Sample | | | | |
|---|---|---|---|---|---|
| | Reference Example 7 100C | Reference Example 8 5C-2 | Reference Example 9 30C-2 | Reference Example 10 60C-2 | Reference Example 11 80C-2 |
| Relative fluorescence intensity | 0.81 | 0.87 | 0.87 | 0.64 | 0.57 |

As is clear from Table 6 and FIG. 6, persimmon leaf extracts (Reference Examples 3 to 11) obtained using purified water by the two-stage extraction method using different temperatures exhibited a lower sugar uptake activity than Reference Example 2 (fraction B). These results suggest that a persimmon leaf extract that exhibits high sugar uptake-promoting activity can be obtained only when persimmon leaves are extracted with an ethyl alcohol-water mixture.

The invention claimed is:

1. A method for treating a human or an animal having a disease selected from the group consisting of diabetes, hyperglycemia, abnormal glucose tolerance, insulin resistance, arteriosclerosis, obesity, dyslipidemia, fat liver and mixtures thereof comprising:

administering to the human or animal having the disease a persimmon leaf extract which is obtained by a process comprising extracting persimmon leaves with a 40-60% ethanol-water mixture to yield an ethanol/water extract of persimmon leaves;

adsorbing the ethanol/water extract of persimmon leaves onto a column packed with an octadecylsilyl-bonded silica gel; and then performing an elution with a 5-10% acetonitrile-water mixture to yield the persimmon leaf extract.

2. A method for treating a human or an animal having a disease selected from the group consisting of diabetes, hyperglycemia, abnormal glucose tolerance, insulin resistance, arteriosclerosis, obesity, dyslipidemia, fat liver and mixtures thereof comprising:

administering to the human or animal having the disease a persimmon leaf extract which is obtained by a process comprising extracting persimmon leaves with a 40-60% ethanol-water mixture to yield an ethanol/water extract of persimmon leaves;

adsorbing the ethanol/water extract of persimmon leaves onto a column packed with a modified dextran; and then performing an elution with a 70-100% methanol/water mixture, or a 60-80% acetone/water mixture to yield the persimmon leaf extract.

* * * * *